United States Patent [19]

Koranek

[11] Patent Number: 4,659,835
[45] Date of Patent: Apr. 21, 1987

[54] PREPARATION OF TETRACHLOROPYRIDINE

[75] Inventor: David J. Koranek, Lake Jackson, Tex.

[73] Assignee: The Dow Chemical Company, Midland, Mich.

[21] Appl. No.: 816,029

[22] Filed: Jan. 3, 1986

[51] Int. Cl.⁴ ............................................. C07D 211/72
[52] U.S. Cl. ..................................................... 546/345
[58] Field of Search ........................................ 546/345

[56] References Cited

U.S. PATENT DOCUMENTS 3,993,654  11/1976  Dean et al. ........................ 546/345

Primary Examiner—Henry R. Jiles
Assistant Examiner—Robert C. Whittenbaugh
Attorney, Agent, or Firm—Joseph T. Majka; Ronald G. Brookens

[57] ABSTRACT

Tetrachloropyridine, more specifically 2,3,5,6-tetrachloropyridine, can be efficiently prepared by reacting pentachloropyridine in water with an oxidizable metal such as zinc, in the absence of an added mineral or organic hydrogen donating acid.

8 Claims, No Drawings

PREPARATION OF TETRACHLOROPYRIDINE

FIELD OF THE INVENTION

This invention relates to a process for preparing tetrachloropyridine, more specifically 2,3,5,6-tetrachloropyridine, from pentachloropyridine (PCP).

BACKGROUND

Various processes are known for preparing tetrachloropyridine from pentachloropyridine. For example, U.S. Pat. No. 4,259,495 discloses a process whereby symmetrical tetrachloropyridine is obtained from pentachloropyridine via zinc reduction in a dialkylalkanephosphonate solvent in the presence of an ammonium salt of an inorganic acid. The process is also described in J. Hetero. Chem., 17, 493 (1980). In U.S. Pat. No. 3,993,654 is described a process for preparing tetrachloropyridine by heating together pentachloropyridine, a mineral or organic hydrogen donating acid and an oxidizable metal such as zinc which combines readily with reactive chlorine.

These known processes suffer the disadvantages in that they require the presence of flammable, toxic or otherwise corrosive substances, including hydrochloric acid, in order to effect the reaction. The use of such substances, in turn, effects a chemical reduction of zinc by the added mineral acid or base. Such chemical reductions can cause reductions in yield due to undesirable by-product formation, such as the dichloropyridines and the trichloropyridines.

SUMMARY OF THE INVENTION

It has been unexpectedly and surprisingly found that tetrachloropyridine, more specifically 2,3,5,6-tetrachloropyridine, can be advantageously prepared by reacting in water, pentachloropyridine with an amount of a metal effective to convert said pentachloropyridine to tetrachloropyridine, said process being conducted in the absence of an added mineral or organic hydrogen donating acid. Preferably the metal is zinc.

DETAILED DESCRIPTION OF THE INVENTION

In general, the invention is practiced, by heating, with agitation, in a closed vessel, particulate pentachloropyridine, water and a particulate oxidizable metal such as zinc. For discussion hereinafter, zinc is cited as a representative metal for illustrating the present invention. The vessel is closed in order that the desired temperature can be reached by confining the water under at least about autogenous pressure. The reaction may be generally illustrated as follows:

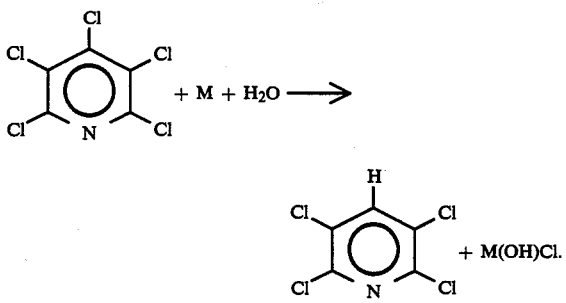

wherein

M is an oxidizable metal such as zinc (Zn), iron (Fe) or magnesium (Mg).

The pentachloropyridine can be in particulate and dispersed form during the reaction and should be stirred or agitated in order to prevent the particles, when they become softened or molten, from agglomerating. The PCP may be first particulated and then dispersed in the aqueous medium or carrier prior to being heated to a softened or molten condition. The PCP can be particulated by grinding or by shearing. Alternatively, the PCP can be heated to its softened or molten condition before addition to the aqueous medium or carrier. The PCP may also be added in its particulate, softened or molten condition to the aqueous medium in the reaction vessel and stirred and heated at the same time, in which case a strong agitation, such as by a stirrer having a power input of at least about 0.005 horsepower/gallon, preferably at least about 0.015 horsepower/gallon, has been found to be particularly advantageous. Any suitable high-intensity agitator, such as a Kenics mixer or a high-shear recycling pump can be employed.

The temperature at which the PCP is reacted with the oxidizable metal may be from about 85° C. on up to about 200° C. or more. Since the reaction works well at temperatures at which the PCP is molten, then a temperature of 100°–145° C. is preferred. Temperatures higher than 145° C. may be used, but such higher temperatures create higher autogenous pressure which require more expensive vessels to contain such pressures. Higher temperatures and pressures are more easily accommodated in a tube-type or coil reactor, useful in continuous flow reactions. Higher temperatures also have the advantage of allowing use of large particle size metal dust and still completing conversion of all the metal in a reasonable length of time. Greatest zinc efficiency, however, is achieved with decreasing temperatures, for example 100° to 120° C.

The reaction pressure is at least autogenous since the reaction temperature is above the boiling point of water. Pressures greater than autogenous may be generated by adding additional pressure after the other ingredients in the reaction vessel have been brought up to reaction temperature.

The reaction time may vary over a wide range depending on the temperature, the choice of metal and the ratio of ingredients to each other. Reaction times generally are a function of zinc particle size and temperature. The time required to completely react the zinc is a function of both reaction temperature and zinc particle size. As particle size becomes larger, more time is needed to consume the zinc charged to the reactor. For example, at 130° C. it was found that roughly one hour of reaction time was required for each 5 microns of particle diameter. The optimum diameter from both kinetic and zinc efficiency considerations appears to be about 10 microns ($\mu$). The zinc dust can have a minimal particle size ranging between about 1 to about 50$\mu$, preferably between about 7 to about 15 microns. Particulate zinc dust of a 12 micron size can be obtained from Gulf Reduction Company, Houston, Tex. A 7 micron size zinc dust can be obtained from the Gulf Reduction Company in Atlanta, Ga. A 15 micron size zinc dust can be obtained from Meadowbrook Corporation, Spelter, W. Va.

There is an exotherm which is easily controlled in small reactors and tube or coil reactors, but which, in large stirred vessels, should be regulated by heat transfer and by controlling the pressure, and, consequently the temperature.

The oxidizable metal is preferably zinc because it is found to give best results and because it forms metal salts which are relatively easy to recover from the aqueous reaction medium. Other oxidizable metals may be used, however, such as Fe, or Mg.

In one embodiment of the invention, PCP is dispersed in water in particulate, non-molten form by employing high-intensity agitation, such as by a Kenics mixer or by a recycle pump. The so-formed slurry is fed into a reaction vessel and particulate oxidizable metal is added. The vessel is sealed and the mixture is stirred and heated until the desired temperature is reached, which is preferably at least the melting point of the PCP. At the completion of the reaction mineral acid can be added to the reaction mixture to dissolve the water-insoluble metal salts. The chloropyridines are taken up in an inert, water immiscible solvent and the metal salt is separated from the water-immiscible solvent.

In another suitable method, molten PCP is added to a heated slurry of particulate metal in water. The slurry is agitated to disperse the PCP. The reaction mixture is brought to the desired reaction temperature and the reaction is continued at the appropriate rate until completed.

In another embodiment the PCP, water, and zinc are charged to the reactor. The reactor is sealed and the mixture is heated, with strong agitation, until the PCP is sufficiently heated, preferably molten.

For best results in obtaining high conversion of the PCP charged to the reactor, the mole ratio of oxidizable metal to PCP should preferably be in the range of about 0.5 to 1.4, most preferably about 1.0 to 1.2 (moles to moles). The process will operate with more or less of the metal, but if less is used there may not be enough to react with all the PCP; if more is used, there is an increased tendency to cause attack of the chlorine on the PCP in positions other than the fourth position, thereby producing di- and trichloropyridines.

The amount of water used as carrier for the reaction can vary over a wide range. Ordinarily, the weight ratio of water to PCP is as least about 0.4 and can be 15 or more, with the ratio 0.5 to 0.8 being preferred; most preferably a ratio of about 0.7 is preferred. Essentially, there should be enough water to help disperse the PCP and to take up the metal salt formed. Having a large excess of water merely adds to the amount of energy and equipment size required to operate the process and is detrimental to the yield of tetrachloropyridine.

The following examples are prepared to illustrate typical processes of the present invention, but the scope of the invention is not to be considered limited to the specific examples given.

EXAMPLE 1

In a 2-liter Parr reactor equipped with a turbine blade stirrer, thermowell, electrical heating jacket, knockback condenser, and temperature and pressure controller were placed 377 grams (1.5 mole) pentachloropyridine (PCP), 98 grams (1.5 mole) zinc metal as a dust having a nominal average particle diameter of 7 microns, and 420 grams (23 moles) of water. The reactor was sealed, agitation was set at 600 rpm, and the mixture was quickly heated to 130° C. over a period of 25 minutes. The pressure controller was allowed to maintain the autogenous pressure of about 24 psig which, along with heat input controlled by the temperature controller, kept the reactor system at 130° C. After 2 hours, 1000 grams of chilled water was pressured into the reactor with a nitrogen pad. The mixture was allowed to stir for 2 minutes, excess pressure was bled off, the reactor was opened and the contents were poured into 1200 grams of toluene. The organic compounds were extracted into the toluene phase with agitation, the entire mixture was filtered and the resulting filter cake washed with about 500 grams of water and 300 grams of toluene. The toluene and aqueous phases of the filtrate were separated, weighed and analyzed. The filter cake was dried, weighed and analyzed.

Gas chromatographic analysis of the toluene phase indicated 74 percent PCP conversion with about 94 percent selectivity to 2,3,5,6-tetrachloropyridine (symmetrical tetrachloropyridine), 2 percent to 2,3,4,5- and 2,3,4,6-tetrachloropyridine, 3 percent to trichloropyridines and 1 percent to dichloropyridines. Analysis of the aqueous phase and the dried filter cake by standard analytical techniques indicated complete conversion of the zinc to a mixture of zinc chloride and zinc hydroxide.

EXAMPLE 2

A mixture of 190 grams PCP (0.75 mole), 50 grams (0.75 mole) zinc dust (7 microns average particle diameter), 210 grams (12 moles) of water, and 1 gram of toluene was heated to reflux with vigorous agitation in a 500 ml round-bottomed flask fitted with a reflux condenser. After 5 hours at 100±1° C., the product mixture was poured into 600 grams of toluene for extraction as described in Example 1 above. The entire mixture was filtered and the filter cake washed with 250 grams of water and 150 grams of toluene. The phases were separated and analyzed as described above. PCP conversion was 84 percent with about 96 percent selectivity to symmetrical tetrachloropyridine, 2 percent to other tetrachloropyridines, 1.5 percent to trichloropyridines and 0.5 percent to dichloropyridines. Zinc conversion (consumption) was essentially complete.

EXAMPLES 3-6

Table I shows run numbers 1-4, corresponding to Examples 3-6, conducted in essentially the same manner as in Example 1, except that the temperature was varied.

TABLE I

| Run number | 1 | 2 | 3 | 4 |
|---|---|---|---|---|
| Nominal zinc dust particle size (microns) | 12 | 12 | 12 | 12 |
| Molar ratio of zinc:PCP:H$_2$O | 1:1:15 | 1:1:15 | 1:1:15 | 1:1:15 |
| Reaction Temperature (°C.) | 100 | 115 | 130 | 144 |
| Reaction Pressure (psig) | 0 | 11 | 25 | 45 |
| Reaction Time (hr) | 1.8 | 1.7 | 1.9 | 1.9 |
| PCP Conversion (%) | 21 | 55 | 65 | 73 |
| Selectivity to Cl$_4$Pyr (mole %) | 97.6 | 98.0 | 92.9 | 94.7 |

EXAMPLES 7-10

Table II shows run numbers 5-8, corresponding to Examples 7-10, to show the effect, primarily, of employing a zinc dust with a nominal particle size of 7μ.

TABLE II

| Run number | 5 | 6 | 7 | 8 |
|---|---|---|---|---|
| Nominal zinc | 7 | 7 | 7 | 7 |

TABLE II-continued

| Run number | 5 | 6 | 7 | 8 |
|---|---|---|---|---|
| dust particle size (microns) | | | | |
| Molar ratio of zinc:PCP:$H_2O$ | | 1:1:15 | | |
| Reaction Temperature (°C.) | 100 | 115 | 130 | 144 |
| Reaction Pressure (psig) | 0 | 11 | 25 | 45 |
| Reaction Time (hr) | 0.59 | 0.54 | 0.58 | 0.55 |
| PCP Conversion (%) | 16 | 35 | 64 | 75 |
| Selectivity to $Cl_4Pyr$ (mole %) | 95.6 | 95.6 | 95.3 | 94.5 |

EXAMPLES 11-15

Table III shows run numbers 9-13, corresponding to Examples 11-15, to show the effect, primarily, of varying the reaction temperature.

TABLE III

| Run number | 9 | 10 | 11 | 12 | 13 |
|---|---|---|---|---|---|
| Nominal zinc dust particle size (microns) | 12 | 12 | 12 | 12 | 12 |
| Molar ratio of zinc:PCP:$H_2O$ | | | 1:1:15 | | |
| Reaction Temperature (°C.) | 90 | 100 | 115 | 130 | 145 |
| Reaction Pressure (psig) | 0 | 0 | 11 | 25 | 44 |
| Reaction Time (hr) | 48 | 20 | 5 | 3 | 2 |
| PCP Conversion (%) | 72 | 79 | 83 | 77 | 78 |
| Zinc Conversion (%) | 97 | 89 | 94 | 92 | 96 |
| Selectivity (mole %) | | | | | |
| to $Cl_4Pyr$ | 97.5 | 97.8 | 97.6 | 96.0 | 94.9 |
| to $Cl_3Pyr$ | 2.2 | 2.1 | 2.3 | 3.5 | 4.3 |
| to $Cl_2Pyr$ | 0.3 | 0.2 | 0.1 | 0.5 | 0.8 |

EXAMPLES 16-19

Table IV shows run numbers 14-17, corresponding to Examples 16-19, to show the effect, primarily, of varying the reaction temperature and source supply of the zinc dust with a nominal particle size of 15μ from a different source supplier.

TABLE IV

| Run number | 14 | 15 | 16 | 17 |
|---|---|---|---|---|
| Nominal zinc dust particle size (microns) | 15 | 15 | 15 | 15 |
| Molar ratio of zinc:PCP:$H_2O$ | | 1:1:15 | | |
| Reaction Temperature (°C.) | 100 | 115 | (130) | 145 |
| Reaction Pressure (psig) | 0 | 10 | 24 | 45 |
| Reaction Time (hr) | 7 | 4 | 3 | 2 |
| PCP Conversion (%) | 85 | 82 | 80 | 77 |
| Zinc Conversion (%) | 94 | 94 | 94 | 98 |
| Selectivity (mole %) | | | | |
| to $Cl_4Pyr$ | 98.8 | 97.7 | 95.6 | 93.9 |
| to $Cl_3Pyr$ | 1.2 | 2.2 | 3.9 | 5.3 |
| to $Cl_2Pyr$ | — | 0.1 | 0.5 | 0.8 |

EXAMPLES 20-23

Table V shows run numbers 18-21, corresponding to Examples 20-23, to show the effect, primarily of reaction temperature.

TABLE V

| Run number | 18 | 19 | 20 | 21 |
|---|---|---|---|---|
| Nominal zinc dust particle size (microns) | 7 | 7 | 7 | 7 |
| Molar ratio of zinc:PCP:$H_2O$ | | 1:1:15 | | |
| Reaction Temperature (°C.) | 100 | 115 | 130 | 145 |
| Reaction Pressure (psig) | 0 | 11 | 25 | 45 |
| Reaction Time (hr) | 5 | 3 | 2 | 1 |
| PCP Conversion (%) | 84 | 83 | 74 | 75 |
| Zinc Conversion (%) | 99 | 100 | 100 | 100 |
| Selectivity (mole %) | | | | |
| to $Cl_4Pyr$ | 97.9 | 97.8 | 96.1 | 95.6 |
| to $Cl_3Pyr$ | 1.7 | 1.9 | 2.9 | 3.2 |
| to $Cl_2Pyr$ | 0.3 | 0.2 | 0.9 | 1.2 |

EXAMPLES 24-26

Table VI shows run numbers 22-24, corresponding to Examples 24-26, to show the effect, primarily of varying the molar ratio of reactants.

TABLE VI

| Run number | 22 | 23 | 24 |
|---|---|---|---|
| Nominal zinc dust particle size (microns) | 7 | 7 | 7 |
| Reaction Temperature (°C.) | 130 | 130 | 130 |
| Reaction Time (hr) | 0.5 | 0.5 | 0.5 |
| Molar Ratio of Reactants | | | |
| zinc:PCP | 0.5 | 0.75 | 1.0 |
| $H_2O$:PCP | 15 | 15 | 15 |
| PCP Conversion (%) | 36 | 52 | 68 |
| Selectivity (mole %) | | | |
| to $Cl_4Pyr$ | 97.8 | 96.9 | 95.0 |
| to $Cl_3Pyr$ | 1.9 | 2.5 | 2.9 |
| to $Cl_2Pyr$ | 0.3 | 0.6 | 2.1 |

EXAMPLES 27-31

Table VII shows run numbers 25-28, corresponding to Examples 27-31, to show the effect, primarily, of varying the water concentration.

TABLE VII

| Run number | 25 | 26 | 27 | 28 |
|---|---|---|---|---|
| Nominal zinc dust particle size (microns) | 12 | 12 | 12 | 12 |
| $H_2O$:PCP mole ratio | 5.3 | 9.3 | 15.3 | 19.3 |
| Reaction Temperature (°C.) | 130 | 130 | 130 | 130 |
| Reaction Time (hr) | 4 | 2 | 2 | 2 |
| PCP Conversion (%) | 68 | 80 | 72 | 55 |
| Zinc Conversion (%) | 87 | 96 | 92 | 84 |
| Selectivity (mole %) | | | | |
| to $Cl_4Pyr$ | 95.2 | 96.0 | 95.8 | 93.8 |
| to $Cl_3Pyr$ | 4.1 | 3.5 | 3.3 | 4.8 |
| to $Cl_2Pyr$ | 0.5 | 0.5 | 0.9 | 1.4 |

What is claimed is:

1. A process for preparing tetrachloropyridine comprising reacting in water, pentachloropyridine with an amount of a metal effective to convert said pentachloropyridine to tetrachloropyridine, said process being conducted in the absence of an added mineral or organic hydrogen donating acid.

2. The process of claim 1 wherein said tetrachloropyridine is 2,3,5,6-tetrachloropyridine.

3. The process of claim 1 wherein said metal is zinc.

4. The process of claim 1 conducted at a temperature of between about 90° C. to about 160° C.

5. The process of claim 1 conducted at a temperature of between about 100° C. to about 145° C.

6. The process of claim 3 wherein the zinc is a dust having a nominal particle size between about 7 microns to about 15 microns.

7. The process of claim 1 conducted with 1 part pentachloropyridine and between about 0.5 to about 1.4 parts zinc on a molar basis.

8. The process of claim 1 conducted with 1 part pentachloropyridine and between about 0.4 to about 20 parts water on a weight basis.

* * * * *